United States Patent [19]

Anderson et al.

[11] 4,225,235

[45] Sep. 30, 1980

[54] SAMPLE INTRODUCTION SYSTEM FOR FLAMELESS EMISSION SPECTROSCOPY

[75] Inventors: Robert J. Anderson, Villa Park; Robert M. Studholme, Tustin, both of Calif.

[73] Assignee: Beckman Instruments, Inc., Fullerton, Calif.

[21] Appl. No.: 922,938

[22] Filed: Jul. 10, 1978

[51] Int. Cl.² .............................................. G01J 3/34
[52] U.S. Cl. .................................................... 356/316
[58] Field of Search ......................... 356/311, 312, 316

[56] References Cited

U.S. PATENT DOCUMENTS

| 3,467,471 | 9/1969 | Greenfield et al. | 356/316 |
| 4,148,612 | 4/1979 | Taylor et al. | 356/316 |
| 4,150,951 | 4/1979 | Capella et al. | 23/232 E |

OTHER PUBLICATIONS

"Analysis of Solution Samples by Microwave Induced Plasma Excitation", Lichte et al.; Anal. Chem., vol. 45 #2; Feb. 1973, pp. 399–401.
"Characteristics of Low Wattage Microwave Induced Argon Plasmas in Metal Excitation;" Runnels et al.; Anal. Chem.; vol. 39#12; Oct. 1967, pp. 1398–1405.
"Emission Spectrometry of Solutions with a Low-Wattage Microwave Discharge", Kawaguchi et al.; Spectrochimica Acta; vol. 27B, pp. 205–210; 1972.

*Primary Examiner*—Vincent P. McGraw
*Attorney, Agent, or Firm*—R. J. Steinmeyer; Robert R. Meads

[57] ABSTRACT

In a system for analyzing the elemental or molecular composition of a sample wherein the sample components are excited through collision with an active metastable gaseous species, the excited sample components emitting a characteristic wavelength of light which may be detected, the system including a microwave cavity through which the gaseous species flows and a microwave source coupled to the cavity, the microwave discharge exciting the gaseous species, there is disclosed an improved liquid sample introduction system which causes complete vaporization and disassociation of the sample. The sample is preferably aspirated directly into the microwave discharge within which the active gas is generated. A novel sample and gas injection probe is also disclosed.

21 Claims, 1 Drawing Figure

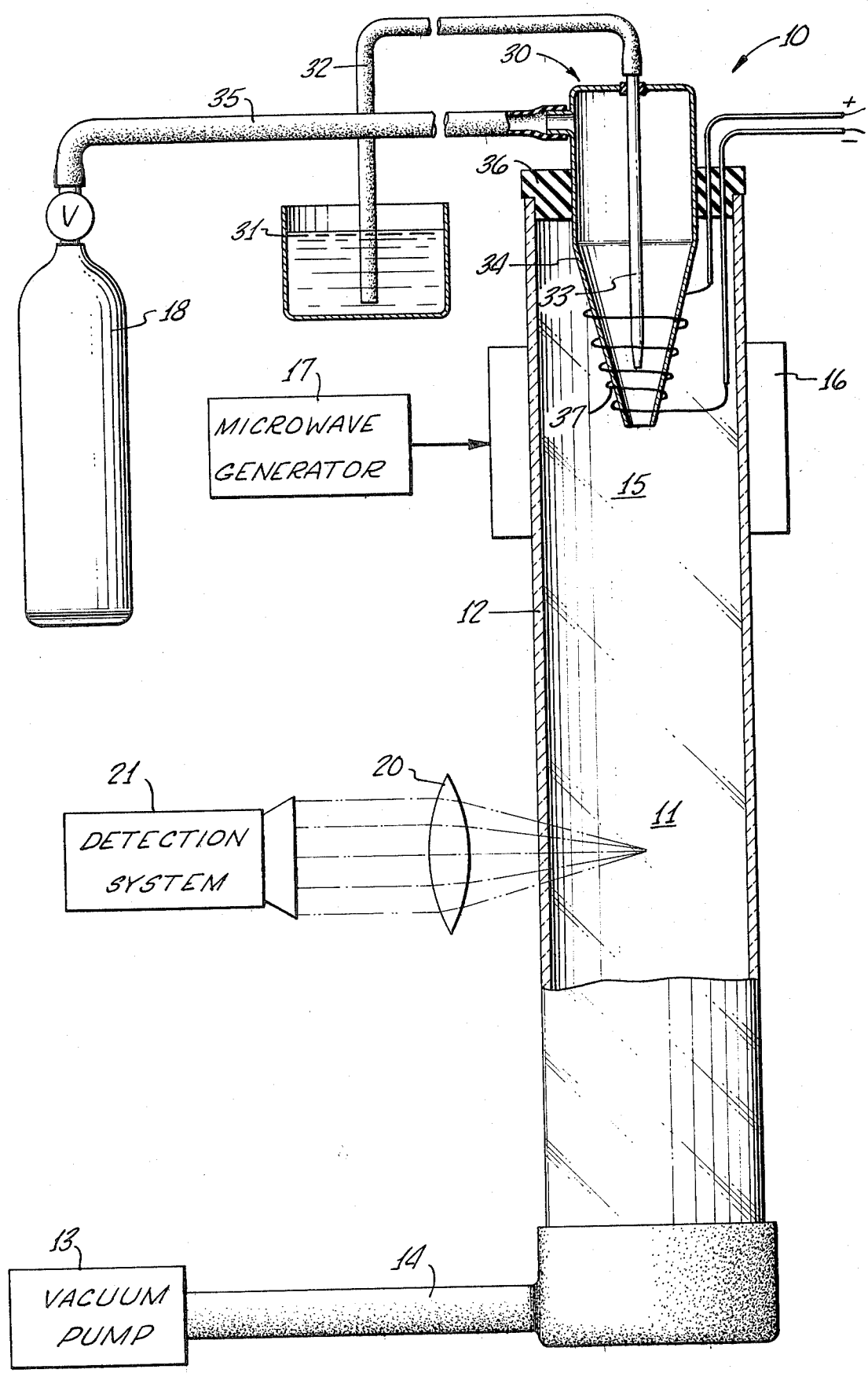

SAMPLE INTRODUCTION SYSTEM FOR FLAMELESS EMISSION SPECTROSCOPY

BACKGROUND OF THE INVENTION

1. Field of the Invention

The present invention relates to flameless emission spectroscopy and, more particularly, to a sample introduction system for flameless emission spectroscopy which causes complete vaporization and disassociation of a sample.

2. Description of the Prior Art

A variety of methods and systems exist for the quantitative and qualitative detection and analysis of atomic and molecular species in samples, such as body fluids. Two of the more common techniques are emission flame photometry and atomic absorption photometry. In emission flame photometry, the sample is aspirated into a propane flame. The metal ions in the sample absorb heat and are raised to an excited state, the excess energy then being emitted in the form of light as the ions relax to their ground state. The wavelength and intensity of the emitted light are determinative respectively of the identity and concentration of the metallic ions present.

In atomic absorption photometry, a hollow cathode lamp containing the element to be analyzed emits light characteristic of the metallic species. The sample is sprayed into a flame and the light emitted by the hollow cathode lamp is passed through the flame. Neutral metallic species in the flame then absorb the light from the hallow cathode lamp, the amount of light absorbed indicating the concentration of the metallic species being determined. The metallic species currently analyzed by these techniques include sodium, potassium, lithium, calcium, and magnesium.

The principal disadvantage of these and other techniques used for the analysis of the composition of a sample is that the detection apparatus must isolate the light emitted by the sample components against the background of the light emitted by the flame, the latter being substantially greater in intensity. Because of the high intensity of the background light, these techniques have been limited to relatively high concentrations of the sample species.

In order to eliminate this disadvantage, another method has recently been developed for analyzing the elemental or molecular composition of a sample. This technique involves the excitation of the sample atoms through collision with an active metastable gaseous species in a Lewis-Rayleigh afterglow, the excited atoms then emitting characteristic wavelengths of light as they relax back to their ground state. Specifically, the sample to be analyzed is introduced into a gas stream containing an excess of an active metastable species of nitrogen or other noble gas whereupon the material, if atomic, is rapidly and repeatedly excited or, if molecular, is decomposed and certain component atoms of the molecule are excited, the excited species emitting characteristic wavelengths of light. The wavelength and intensity of the emitted light are determinative respectively of the identity and concentration of the atoms of the different elements present.

There are at least two advantages to this technique. The first of these is that upon relaxation to the ground state, the atoms may collide again with an active nitrogen molecule, providing that the active nitrogen is present in excess, thereby reexciting the atom with a subsequent reemission of a characteristic photon. This permits this technique to be used with very low concentrations of atoms. The second advantage is that in contrast to flame photometry or atomic absorption photometry, the background radiation in the Lewis-Rayleigh afterglow region is extremely low in the visible and ultraviolet, permitting the characteristic emission spectra to be observed against a black background. These two advantages combine to make this technique extremely sensitive and capable of extremely good linearity. As a result, a number of systems have been developed utilizing this technique.

When designing a system incorporating this technique, a number of factors must be carefully considered to insure that an accurate result is obtained. Initially, it is necessary to introduce a liquid sample into the discharge chamber in such a way that the sample is completely vaporized and maintained in the gas phase. If a portion of the sample is incompletely vaporized and remains on the sample introduction probe or other means, this portion of the sample may be carried over to a subsequent test and provide an inaccurate result in the subsequent test. In addition, where the introduced sample is molecular, it is necessary to totally disassociate the molecular sample into its atomic components. This is necessary so that the component atoms can be excited into fluorescence. In systems suggested heretofore, one or the other or both of these factors have been inadequately accounted for with the result that the systems have not produced the desired results.

SUMMARY OF THE INVENTION

According to the present invention, there is provided a method and apparatus for analyzing the elemental or molecular composition of a sample utilizing the technique of flameless emission spectroscopy which solves these problems in a manner unknown heretofore. More particularly, the present invention relates to a fluid sample introduction system for flameless emission spectroscopy which assures complete disassociation of a sample. For this purpose, a novel sample injection probe is described. Furthermore, the sample and the carrier gas pass through the microwave discharge and the high electron energy of the discharge insures complete disassociation of the sample. Preferably, both results are achieved by aspirating the sample directly into the microwave cavity in which the active nitrogen itself is generated. Since the cavity operates at a frequency of typically 2.45 GHz, a liquid sample is instantly vaporized and disassociated. Thus, both vaporization of a liquid sample and generation of active nitrogen are accomplished within the same microwave cavity, observation of the emission spectrum being accomplished several inches away from the microwave discharge in the region of the Lewis-Rayleigh afterglow.

It is therefore an object of the present invention to provide a sample introduction system for flameless emission spectroscopy.

It is a further object of the present invention to provide a sample introduction system for flameless emission spectroscopy which insures complete vaporization of a liquid sample.

It is a still further object of the present invention to provide a sample introduction system for flameless emission spectroscopy which insures complete disassociation of a molecular sample into its component atoms.

It is another object of the present invention to provide a system for flameless emission spectroscopy in which a sample is aspirated directly into the microwave cavity wherein an active metastable gaseous species is generated.

Still other objects, features, and attendant advantages of the present invention will become apparent to those skilled in the art from a reading of the following detailed description of the preferred embodiment constructed in accordance therewith, taken in conjuction with the accompanying drawings wherein:

BRIEF DESCRIPTION OF THE DRAWINGS

The sole FIGURE is a partially schematic, partially sectional side view of a flameless emission spectroscopic system for analyzing the elemental or molecular composition of a sample incorporating a sample introduction system constructed in accordance with the teachings of the present invention.

DESCRIPTION OF THE PREFERRED EMBODIMENT

Referring now to the drawing, the present system, generally designated 10, for flameless emission spectroscopy includes a reaction chamber 11 preferably formed from a length of fused silica tubing 12 which is maintained at some low pressure, preferably between 1 and 10 torr, by means of a vacuum pump 13 connected to one end of tubing 12 by a length of rubber tubing 14. The length of tubing 12 is insignificant and the diameter may be approximately 10 mm. A microwave chamber 15 is formed within tubing 12 by surrounding tubing 12 with a microwave cavity 16 which is coupled to a microwave generator 17, the latter preferably operating at 2.45 GHz. Generally speaking, nitrogen or some other suitable inert gas is fed from a gas bottle 18 into chamber 15 where energy is coupled thereto from generator 17, causing the molecules to be raised to an active electronic excited state. The amount of active nitrogen produced is a function of microwave power, pressure, flow rate, and nitrogen purity.

If a sample is forced into the gas phase and mixed with the active nitrogen, the material, if atomic, is rapidly and repeatedly excited or, if molecular, is disassociated into its component atoms and these atoms are rapidly and repeatedly excited. In either case, the atoms present in the sample emit light at specific wavelengths whereupon the wavelengths are determinative of the identity of the atoms and the intensity of the emitted light at each wavelength is determinative of the concentration of the atom present. At a fixed distance of approximately 5–30 cm downstream of microwave cavity 16, in the area known as the Lewis-Rayleigh afterglow region, the fluorescence is monitored to determine the wavelengths and corresponding intensities to establish the identity and concentrations of the elements present. The emitted light may be collected by a collection optics system, generally designated 20, which focuses the light into a detection system 21 that measures the light intensity at the wavelengths of interest.

Where the molecular composition of a sample is desired, it is possible to space detection system 21 from cavity 16 by an amount which will permit recombination of the atoms into molecules whereupon the molecules will collide with the active nitrogen and emit light at a wavelength characteristic of the molecule. Thus, system 10 can be used either for elemental or molecular analysis.

System 10 may be advantageously used to analyze various components in body fluids or other liquids. In the case of a liquid sample, it is necessary to introduce the sample into system 10 in such a way that the molecules are completely disassociated into their atomic components and the atomic components completely vaporized. This is achieved with the present sample introduction system, generally designated 30.

In sample introduction system 30, the sample is first diluted, such as with water, in a beaker 31, for example. Beaker 31 receives one end of a length of tubing 32, the other end of which is connected to one end of a tiny capillary tube 33. The other end of tube 33, the tip, extends into tubing 12. Tube 33 is preferably made from a metallic or a ceramic material and has a preferred diameter in the range of from 0.001 to 0.01 inches. Tube 33 is positioned within a second metallic or ceramic tube 34, one end of which, the tip, extends beyond the tip of tube 33 and is tapered to a small diameter. The tip of tube 34 preferably extends beyond the tip of tube 33 by approximately 1–2 mm and tapers down to a diameter in the range of from 0.005 to 0.03 inches. The other end of tube 34 is connected by a length of tubing 35 to gas bottle 18.

Tube 34, with capillary tube 33 inside thereof, may be positioned within a plug 36 which extends into the end of tubing 12 opposite from the end connected to pump 13. A heating coil 37 surrounds tube 34, adjacent the tip thereof, to heat tube 34 and tube 33 therein. The leads from coil 37 extend through plug 36 for connection to a suitable source of voltage.

With the construction just described, the liquid sample is aspirated into extremely small droplets by allowing the sample to flow through tube 33, which has a very small diameter, across the output tip of which a stream of dry nitrogen gas is being blown. Furthermore, the tips of tubes 33 and 34 are heated and suspended down into tubing 12. Such a construction results in complete vaporization of the sample and insures an absence of sample carryover from one test to another.

According to the present invention, the sample is injected into the carrier gas and the carrier gas and the sample are conducted through the discharge in cavity 16. According to the best mode contemplated for carrying out the principles of the present invention, the tip of tube 34 extends into chamber 15 so that the sample is aspirated directly into the microwave discharge within which the active nitrogen is generated. Since the cavity operates at a high frequency, the water in which the sample is diluted and the sample itself absorb microwave energy and are instantly vaporized. Furthermore, the energy of the discharge causes the sample molecules to become disassociated into their component atoms.

It is, therefore, a first teaching of the present invention to utilize system 30 to inject the carrier gas and a liquid sample through heated coaxial tubes to effect complete vaporization of the sample. System 30 may also be used for gaseous or solid samples which may be put into solution or gaseous samples may be introduced directly via tube 33. It is another teaching of the present invention to position system 30 upstream of the discharge in cavity 16 so that the energy in chamber 15 is utilized to disassociate the gaseous sample into its component atoms.

It is a further teaching of the present invention to aspirate the sample directly into the microwave discharge within which the active nitrogen is generated. In this latter case, the energy in the discharge insures complete vaporization and disassociation of a sample, even without sample introduction system 30, although sample introduction system 30 is preferred. However, other sample introduction systems can be used under these circumstances. For example, the sample solution can be injected through a very small capillary tube onto a hot wire within chamber 15.

Upon mixing of the sample gas with the active nitrogen, the excited gaseous species collides with the active nitrogen species to excite the gaseous species. Upon relaxation to the ground state, the gaseous species emits a characteristic photon at specific wavelengths. The emitted light is collected by collection optics 20 which focuses the light into detection system 21.

A typical detection system, known to those skilled in the art, consists of collection lenses, a monochromator, a vidicon detector, and a multichannel analyzer. Optics 20 focuses the light from within chamber 11 onto the input slit of the monochromator. The vidicon detector is located in the focal plane of the monochromator grating, at the normal location of the output slit. The vidicon detector has an array of small photodiodes, each of which therefore views a small portion of the spectrum. The multichannel analyzer displays an output whose amplitude is proportional to the light intensity on each of the photodiodes, resulting in a spectrum of the amplitude of the light intensity as a function of wavelength. Since each of the gaseous species emits light at a specific wavelength, by monitoring the amplitude of the intensity at a specific photodiode, or by summing over several diodes, the concentration of the various species can be determined.

Since the entire spectrum is observed continuously during the passage of the sample through reaction chamber 11, the concentration of a number of different species can be determined simultaneously, from a single sample, during a short period of time on the order of a few seconds to a minute.

The amplitude of the emitted light at a particular wavelength is, therefore, proportional to the instantaneous concentration of a given species within reaction chamber 15 at that time. In order to relate this to the concentration of the species in the original sample, system 10 must be calibrated and a variety of different techniques for calibration have been taught in the prior art. For example, a test can be performed with a standard having a known concentration of a given species and the detected output used to calibrate the system. Alternatively, the standard could be put into the diluent for the sample and the concentration of the standard determined simultaneously with the concentration of the unknowns in the sample.

It can therefore be seen that according to the present invention, there is provided a method and apparatus for analyzing the elemental or molecular composition of a sample utilizing the technique of flameless emission spectroscopy which solves the problems encountered heretofore. More particularly, the present invention relates to a liquid sample introduction system for flameless emission spectroscopy which assures complete vaporization and disassociation of a sample. For this purpose, a novel sample injection probe consisting of tubes 33 and 34 causes complete vaporization of the sample. Furthermore, the sample and the carrier gas pass through the microwave discharge and the high electron energy of this discharge insures complete disassociation of the sample. Preferably, both results are achieved by aspirating the sample directly into microwave cavity 16 where the active nitrogen is generated. Observation of the emission spectrum is accomplished several inches away from the microwave discharge in the region of Lewis-Rayleigh afterglow.

While the invention has been described with respect to a preferred physical embodiment constructed in accordance therewith, it will be apparent to those skilled in the art that various modifications and improvements may be made without departing from the scope and spirit of the invention. Accordingly, it is to be understood that the invention is not to be limited by the specific illustrative embodiment, but only by the scope of the appended claims.

We claim:

1. In a system for analyzing the composition of a fluid sample wherein the sample components are excited through collision with an active metastable gaseous species, the excited sample components emitting a characteristic wavelength of light which may be detected, said system including a microwave cavity through which said gaseous species flows and a microwave source coupled to said cavity, said source and said cavity exciting said gaseous species, a method comprising:
   aspirating said sample directly into said microwave cavity to cause complete disassociation of said sample.

2. In a system according to claim 1, wherein said sample is in solution, a method further comprising:
   positioning a heating means in said microwave cavity for heating said sample to vaporize same.

3. In a system according to claim 1, wherein said sample is in solution, a method further comprising:
   positioning a filament in said microwave cavity for heating said sample to vaporize same.

4. In a system according to claim 3, a method further comprising:
   positioning a capillary tube with one end thereof extending into said microwave cavity for aspirating said sample onto said filament; and
   conducting said sample into the other end of said tube.

5. In a system for analyzing the composition of a fluid sample wherein the sample components are excited through collision with an active metastable gaseous species, the excited sample components emitting a characteristic wavelength of light which may be detected, said system including a chamber through which said gaseous species flows, a microwave cavity surrounding said chamber, and a microwave source coupled to said cavity, said source and said cavity exciting said gaseous species, the improvement comprising:
   means for aspirating said sample directly into said microwave cavity to cause complete disassociation of said sample.

6. In a system according to claim 5, the improvement wherein:
   said aspirating means is further operative to introduce said gaseous species into said cavity.

7. In a system according to claim 6, the improvement wherein said aspirating means comprises:
   a first tube for conducting said sample into said cavity; and a second tube positioned coaxially with and surrounding said first tube for conducting said gaseous species into said cavity, the ends of said first and second tubes in said cavity being closely adjacent to each other whereby said sample enters the flow of said gaseous species as it emerges from said first tube.

8. In a system according to claim 7, the improvement further comprising:
  means for heating said end of said second tube in said cavity.

9. In a system according to claim 8, the improvement wherein said end of said second tube extends beyond said end of said first tube.

10. In a system for analyzing the composition of a sample wherein the sample components are excited through collision with an active metastable gaseous species, the excited sample components emitting a characteristic wavelength of light which may be detected, said system including a chamber through which said gaseous species flows, a microwave cavity surrounding said chamber, and a microwave source coupled to said cavity, said source and said cavity exciting said gaseous species, means for introducing a liquid sample and said gaseous species into said chamber comprising:
  a first tube, one end of said first tube receiving said liquid sample, the other end of said first tube extending into said chamber;
  a second tube positioned coaxially with and surrounding said first tube, one end of said second tube receiving said gaseous species, the other end of said second tube being positioned adjacent to said other end of said first tube whereby said sample enters the flow of said gaseous species as it emerges from said other end of said first tube; and
  means for heating said other end of said second tube to vaporize said sample.

11. In a system according to claim 10, the improvement wherein:
  said first tube is made from a metallic or a ceramic material.

12. In a system according to claim 10 or 11, the improvement wherein:
  said second tube is made from a metallic or a ceramic material.

13. In a system according to claim 10, the improvement wherein:
  said first tube has an inside diameter in the range of from approximately 0.001 to approximately 0.01 inches.

14. In a system according to claim 10 or 13, the improvement wherein:
  said other end of said second tube extends beyond said other end of said first tube.

15. In a system according to claim 14, the improvement wherein:
  said other end of said second tube extends beyond said other end of said first tube by approximately 1–2 mm.

16. In a system according to claim 14, the improvement wherein:
  said other end of said second tube has an inside diameter in the range of from approximately 0.005 to approximately 0.03 inches.

17. In a system according to claim 10, the improvement wherein said heating means comprises:
  a heating coil surrounding said other end of said second tube.

18. In a system according to claim 17, the improvement wherein:
  said coaxial first and second tubes are positioned upstream of said microwave cavity.

19. In a system according to claim 10, the improvement wherein:
  said other end of said second tube extends into said microwave cavity.

20. In a system for analyzing the composition of a sample wherein the sample components are excited in a chamber through collision with an active metastable gaseous species, the excited sample components emitting a characteristic wavelength of light, said system including a microwave cavity surrounding said chamber and a microwave source coupled to said cavity, means for introducing said sample into said chamber comprising:
  first and second coaxial tubes, first ends of which extend into said reaction chamber;
  means for heating said first ends of said tubes; and
  means for conducting said sample and said gaseous species into the other ends of said tubes.

21. In a system according to claim 20, the improvement wherein:
  said first tube is positioned within said second tube, said sample is conducted into said first tube, and said gaseous species is conducted into said second tube.

* * * * *